United States Patent [19]

Connor et al.

[11] Patent Number: 5,240,929
[45] Date of Patent: Aug. 31, 1993

[54] 2-HETEROCYCLIC-5-HYDROXY-1,3-PYRIMIDINES USEFUL AS ANTIINFLAMMATORY AGENTS

[75] Inventors: David T. Connor, Ann Arbor; Catherine R. Kostlan, Saline; Paul C. Unangst, Ann Arbor, all of Mich.

[73] Assignee: Warner-Lambert Company, Morris Plains, N.J.

[21] Appl. No.: 924,212

[22] Filed: Aug. 3, 1992

[51] Int. Cl.$^5$ .............. A61K 31/505; C07D 403/04; C07D 413/04; C07D 417/04
[52] U.S. Cl. ..................................... 514/269; 544/298
[58] Field of Search ........................ 514/269; 544/298

[56] References Cited

U.S. PATENT DOCUMENTS 4,636,516  1/1987  Kubo et al. .................. 514/365

*Primary Examiner*—John M. Ford
*Attorney, Agent, or Firm*—Ronald A. Daignault

[57] ABSTRACT

The present invention is novel compounds which are 2-heterocyclic-4,6-ditertiarybutyl-5-hydroxy-1,3-pyrimidines, where heterocyclic is selected from imidazole, thiazole, and oxazole, and pharmaceutically acceptable additional salts, bases, and base salts thereof, pharmaceutical compositions and methods of use therefor. The invention compounds are found to have activity as inhibitors of 5-lipoxygenase and/or cyclooxygenase providing treatment of, for example, preferably inflammation.

7 Claims, No Drawings

2-HETEROCYCLIC-5-HYDROXY-1,3-PYRIMIDINES USEFUL AS ANTIINFLAMMATORY AGENTS

BACKGROUND OF THE INVENTION

The present invention is related to novel compounds which are 2-heterocyclic-5-hydroxy-1,3-pyrimidines and pharmaceutically acceptable acid addition or base salts thereof, pharmaceutical compositions and methods of use therefor. Particularly the invention is related to 2-thiazole, 2-oxazole, or 2-imidazole-5-hydroxy-1,3-pyrimidines. The invention compounds have activity as inhibitors of 5-lipoxygenase and/or cyclooxygenase providing treatment of conditions advantageously affected by such inhibition including, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants and as inhibitors of LDL into macrophages. However, overall the preferable use is to treat inflammatory conditions. Thus, the present invention is also a pharmaceutical composition or method of manufacturing a pharmaceutical composition for the use of treating the noted conditions.

3,5-Di-tertiary-butyl-4-hydroxybenzene, substituted by thiazoles, oxazoles, and imidazoles are known to provide antiinflammatory activity, U.S. Pat. No. 4,636,516. 2-Substituted-5-hydroxy-1,3-pyrimidines as antiinflammatory agents are also described as copending U.S. application Ser. Nos. 07/648,115 of Jan. 31, 1991, and 07/756,400 of Sep. 9, 1991, respectively.

SUMMARY OF THE INVENTION

Accordingly the present invention is a compound of the Formula I

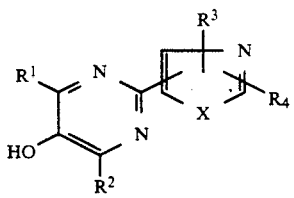

or a pharmaceutically acceptable salt or hydrate thereof, wherein X is NH, S or O; $R_1$ and $R_2$ are each independently hydrogen or lower alkyl; $R_3$ is hydrogen, lower alkyl, phenyl, substituted phenyl, $NR_5R_6$ in which $R_5$ and $R_6$ are each independently hydrogen or lower alkyl, $OR_7$ or $S(O)_nR_7$ in which $R_7$ is hydrogen, lower alkyl, or phenyl and n is 0, 1, or 2; and $R_4$ is phenyl, substituted phenyl, $NR_5R_6$, $OR_7$, or $S(O)_nR_7$ in which $R_5$, $R_6$, and $R_7$ are as defined above.

The present invention is also a pharmaceutical composition for the treatment of conditions advantageously affected by the inhibition of one or both of 5-lipoxygenase and cyclooxygenase which comprises an amount effective for the treatment of the condition of a compound of the Formula I and the pharmaceutically acceptable acid addition or base salt thereof together with a pharmaceutically acceptable carrier. The condition is meant to include, for example, a condition as listed above which is advantageously affected by such inhibition of one or both of 5-lipoxygenase and cyclooxygenase, preferably, arthritis or other inflammatory diseases, allergic diseases, pain, fever, and psoriasis, but more preferably inflammatory conditions or diseases.

The present invention is also a method for treatment of the condition as noted above in a mammal, including humans, suffering therefrom with a compound of the Formula I or the pharmaceutically acceptable acid addition or base salt thereof, in unit dosage form. The invention also provides for use of any such compound of Formula I or salt thereof in the manufacture of medical therapeutic agent.

Pharmaceutical composition or use of the compound or salt of Formula I is meant to include treatment understood to be prophylactic pertinent to the foregoing named condition.

Preferred compounds of the present invention are compounds of the Formula I wherein $R_1$ and $R_2$ are tertiarybutyl and $R_4$ is OH.

DETAILED DESCRIPTION OF THE INVENTION

In the compounds of Formula (I) the term "lower alkyl" includes an alkyl group of from one to six carbons such as methyl, ethyl, propyl, butyl, and the like and isomers thereof.

Halogen is chloro, bromo, or fluoro.

Substituted phenyl includes one, two, or three substituents of one or more of each of alkyl of one to four carbons, inclusive, alkoxy, thioalkoxy, alkanoyloxy, carboalkoxy, in which "alk" is defined as lower alkyl above, hydroxymethyl, $NR_5R_6$ wherein $R_5$ and $R_6$ are each independently as defined above, or nitro, $CF_3$, or halogen as defined above.

The compounds of the invention may contain geometric isomers. Thus, the invention includes the individual isomers and mixtures thereof. The individual isomers may be prepared or isolated by methods known in the art.

A tautomeric form of selected compounds of Formula I would be recognized by an ordinarily skilled artisan to be within the present invention.

Appropriate compounds of Formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfonate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric or optical isomers. Thus, the invention includes the individual isomers and mixtures thereof. The individual isomers may be prepared or isolated by methods known in the art.

The compounds of the invention may contain an asymmetric carbon atom, particularly, for example, in the side chain of the compounds of Formula I. Thus, the invention includes individual enantiomers, the pure S, the pure R isomer, and mixtures thereof. The individual enantiomers may be prepared or isolated by methods known in the art. Likewise diastereomers are included in the invention if possible, both as individuals or mixtures thereof.

Hydrates of compounds of Formula I, if possible, are also the present invention and are prepared or isolated by conventional methods known to an ordinarily skilled artisan.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula (I) or pharmacologically acceptable salt thereof to achieve a therapeutic effect will, of course, vary both with the particular compound, the route of administration, the mammal under treatment, and the particular disorder or disease concerned. A suitable dose of a compound of Formula (I) or pharmacologically acceptable salt thereof for a mammal suffering from, or likely to suffer from any condition as described hereinbefore is 0.1 $\mu$g-500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng-100 $\mu$g of the compound per kilogram, typically about 0.1 $\mu$g/kg.

In the case of oral dosing for the treatment or prophylaxis of arthritis or inflammation in general, due to any course, a suitable dose of a compound of Formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; NaHPO, 1.15 g; KHPO, 0.2 g; and KCl, 0.2 g/l). Cells are finally suspended in PBS containing 1.0 mM calcium at a density of $2 \times 10$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at $-20°$. Aliquots (100 μL) are analyzed for $LTB_4$ and $PGF_{2\alpha}$ using radioimmunoassay kits as provided by the supplier.

Biochemical data obtained from this whole cell assay may be shown as $IC_{50}s$ which are calculated as the amount of test compound causing 50% inhibition of $LTB_4$ or $PGF_{2\alpha}$ formation. The following Table exemplifies the data for the present invention.

| BIOLOGICAL RESULTS | | |
|---|---|---|
| Compound of | $IC_{50}$ (μM) | |
| Example Number | ARBL | ARBC |
| 1 | 1.18 | 1.35 |

In addition to the compounds of Formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Combinations of a compound of the Formula I and other active ingredients will generally be in the aforementioned ratios.

NSAIDs can be characterized into five groups:

(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-CH_2CH_2COO^-Na^+$), typically attached directly or via a carbonyl function to a ring system, preferably to an aromatic ring system.

The acetic acid derivatives which may be used comprise: indomathacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free $-CH_2COOH$ group (which optionally can be in the form of a pharmaceutically acceptable salt group, e.g. $-CH_2COO^-Na^+$), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

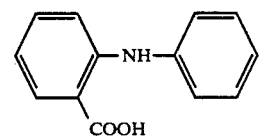

which can bear a variety of substituents and in which the free $-COOH$ group can be in the form of a pharmaceutically acceptable salt group, e.g., $-COO^-Na^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

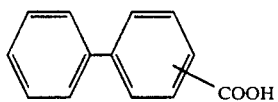

which can bear a variety of substituents and in which the free —COOH group can be in the form of a pharmaceutically acceptable salt group, e.g., —COO—Na+.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

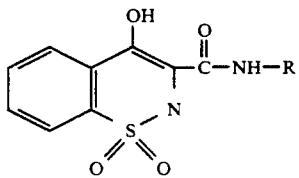

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the Formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the Formula I and their salts are prepared generally by the following processes and constitute a further aspect of the present invention.

First, the compounds of Formula I may be prepared by reaction of an α-halocarbonyl compound 1 with a urea, thiourea, amidine, amide, thioamide, or amidothiocarbonic acid derivative 2.

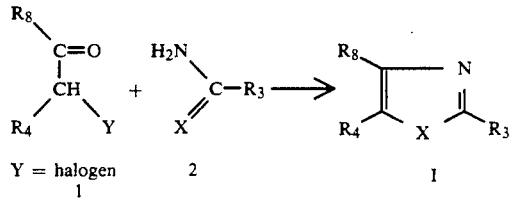

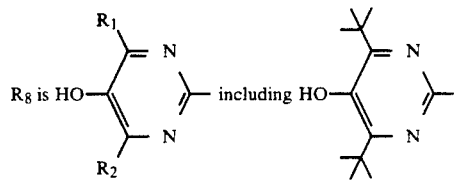

The reaction proceeds in an alcohol, acetone, chloroform, or other suitable solvent at 25° C. to 150° C. for 1 to 24 hours.

A second method is the reaction of an α-aminocarbonyl compound 3 with an isocyanic acid, an isothiocyanic acid, or a lower alkyl derivative, or alkali metal salt of an isocyanic or isothiocyanic acid 4:

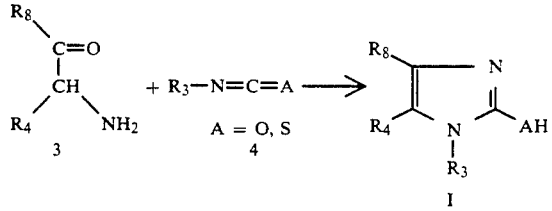

This reaction takes place in an alcohol, aqueous alcohol, or pyridine with or without added mineral acid at 25° C. to 150° C. for 1 to 24 hours.

A third method specifically for synthesizing thiaxoles of Formula I wherein $R_4$ is OH, involves the reaction of an α-thiocarboxylic acid of the formula

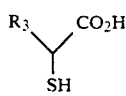

wherein R$_3$ is as defined above with a compound of the formula

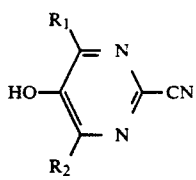

wherein R$_1$ and R$_2$ are defined above. Alternatively an α-bromocarboxylic acid methyl ester may be reacted with a 5-hydroxy-4,6-substituted-pyrimidine-2-thioamide. These reactions proceed at a temperature of 0° C. to 110° C. in the presence of an organic base such as pyridine in a solvent such as toluene.

Finally, thiazoles of Formula I wherein R$_4$ is OH may also be prepared by reacting a compound of the formula

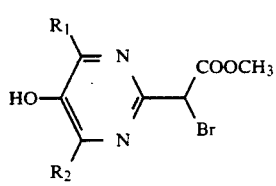

wherein R$_1$ and R$_2$ are defined above with a thioamide

wherein R$_3$ is as defined above. The reaction proceeds at a temperature of 0° C. to 110° C. in the presence of an organic base such as pyridine in a solvent such as toluene.

Under certain circumstances as discussed below, it is necessary to protect the phenolic OH of the pyrimidine ring in various intermediates as shown by the group Q in the following formula

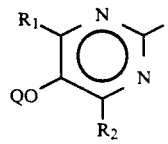

where Q is a suitable oxygen protecting group, preferably methoxyethoxymethyl (MEM).

The MEM group is removed later using 1) Lewis acids such as ZnBr$_2$ in halogenated solvents such as methylene chloride, chloroform, and dichloromethane at 0° to 60° C., 2) mineral acids such as HCl, HBr, or HNO$_3$ in solvents such as water, alkanols, tetrahydrofuran, dialkylethers, dioxane, glyme, diglyme at 0° to 60° C. or 3) organic acids such as acetic acid in the solvents described in 1) and 2) at 0° to 60° C.

Introduction and removal of such suitable oxygen protecting groups are well-known in the art of organic chemistry; see for example "Protective Groups in Organic Chemistry," J. F. W. McOmie, ed., (New York, 1973), pages 43ff, 95ff, J .F .W. McOmie, *Advances in Organic Chemistry*, Vol. 3, 159–190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The starting materials for the present invention are prepared as set out below, and as repeated here from copending U.S. application Ser. Nos. PCT/US 92/00442, 07/648,115 of Jan. 31, 1991, and 07/756,400 of Sep. 9, 1991, which are incorporated by reference, therefor.

Compound of the Formula 3' in Scheme 1 below is prepared from the known haloketone 2' (C. W. Shoppee and D. Stevenson, *J. Chem. Soc. Perkin I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 3' is converted to oxazole 4' by treatment with an ammonium salt such as ammonium chloride or preferably ammonium acetate in a solvent such as acetic acid at reflux for 1 to 16 hours or in a solvent such as formamide at 100° to 200° C. for 1 to 6 hours. Alternatively 2' is converted directly to 4' by treatment with acetamide or ammonium acetate in a solvent such as acetic acid at reflux. The oxazole 4' is converted to pyrimidine 5' by treatment with ammonia or an ammonium salt at elevated temperature. Preferably 4' is reacted with concentrated ammonium hydroxide at 150° to 190° C. in a pressure reaction vessel for 6 to 72 hours. 5' is also prepared by reaction of 3' with an ammonium salt such as NH$_4$Cl or NH$_4$OAc in a solvent such as formamide at a temperature of 180° to 200° C. for longer periods of time such as overnight to 1 week.

SCHEME 1

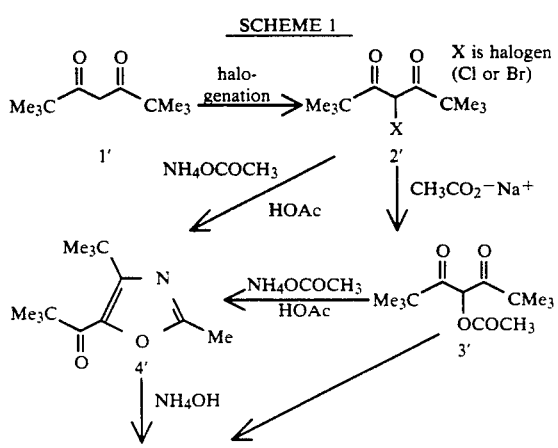

-continued
SCHEME 1

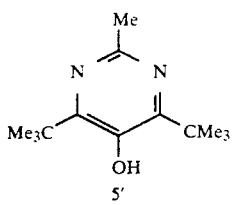
5'

Scheme 2 shows the preparation of the starting material beginning with the compound of the Formula 5' from the preparation shown in Scheme 1.

SCHEME 2

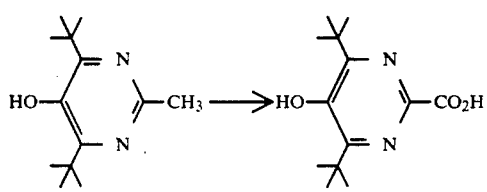

Details of the above conversion are described in PCT/US 92/00442.

By way of specific illustration the following scheme shows the preparation of a representative embodiment of the present invention.

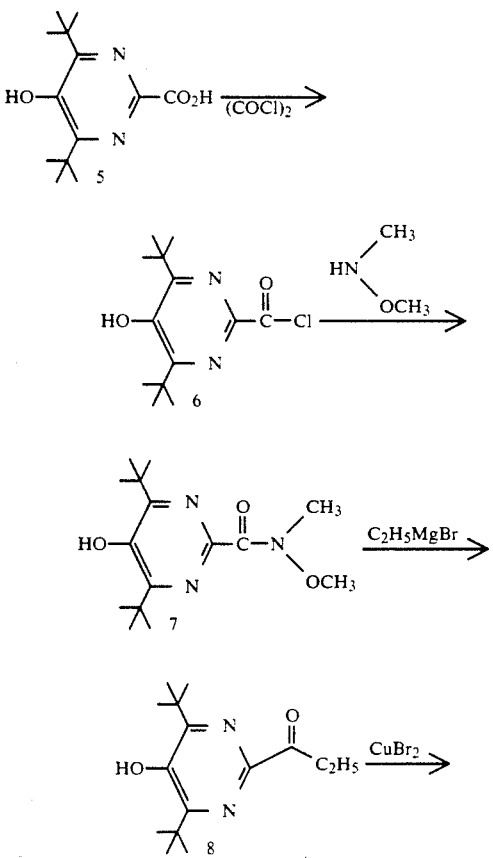

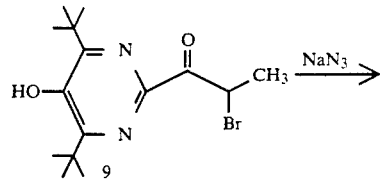

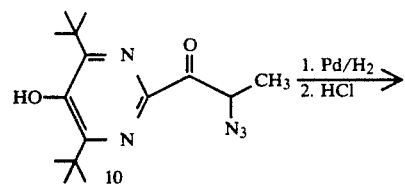

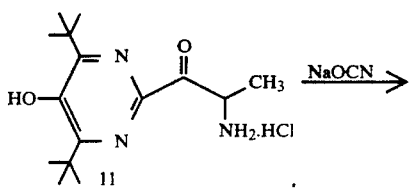

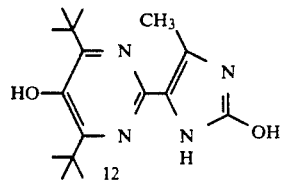

Pyrimidine carboxylic acid 5 (described in PCT/US 92/00442) was converted to the N-methoxy-N-methylamide 7 via the acid chloride 6. Reaction of amide 7 with an ethyl Grignard reagent gave the ethyl ketone 8 (general procedure of S. Nahn and S. M. Weinreb, *Tetrahedron Letters* 22:3815 (1981); other methods of converting carboxylic acids to ketones could be substituted). Bromination of 8 with cuprous bromide ($Br_2$ could also be used) gave the α-bromoketone 9, and treatment of 9 with sodium azide gave the α-azidoketone 10. Catalytic reduction of the azide provided the α-aminoketone 11, and reaction of 11 with sodium cyanate gave the final product 12.

(This procedure in the di-t-butylphenol series is described by Y. Isomura, S. Sakamoto, N. Ito, H. Homma, T. Abe, and K. Kubo, *Chem. Pharm. Bull.* 32:152 (1984)).

EXAMPLE 1

4,6-Bis(1,1-dimethylethyl)-5-hydroxy-N-methoxy-N-methyl-2-pyrimidinecarboxamide

A mixture of 8.4 g (33 mmol) of 4,6-bis(1,1-dimethylethyl)-5-hydroxy-2-pyrimidinecarboxylic acid and 0.50 mL (0.47 g, 6.5 mmol) of N,N-dimethylformamide in 120 mL of dichloromethane was cooled in ice and treated dropwise with a solution of 4.9 mL (7.1 g, 56 mmol) of oxalyl chloride in 18 mL of dichloromethane. The mixture was stirred with ice cooling for 2 hours, then filtered, and evaporated. The residual crude acid chloride was redissolved in 85 mL of dichloromethane and added dropwise to an ice-cooled mixture of 4.0 g (41 mmol) of N,O-dimethylhydroxylamine hydrochloride and 15 mL (12.2 g, 123 mmol) of 1-methylpiperidine in 150 mL of dichloromethane. The mixture was stirred at room temperature for 16 hours, then washed with 0.4N hydrochloric acid, brine, 5% aqueous sodium bicarbonate, and brine again. The organic layer was dried (anhydrous sodium sulfate) and evaporated, and the residue recrystallized from ethyl acetate/hexane to yield 6.4 g (65%) of the amide product, mp 140° C.–142° C.

$^1$H NMR (dimethyl sulfoxide-$d_6$): δ 1.40 (s, 18 H, t-Bu), 3.25 (s, 3 H, NH$_3$), 3.67 (s, 3 H, OCH$_3$), 8.43 (broad s, 1 H, OH).

Anal Calcd. for $C_{15}H_{25}N_3O_3$:
C, 60.99; H, 8.53; N, 14.23.
Found: C, 61.16; H, 8.89; N, 14.38.

EXAMPLE 2

1-[4,6-Bis(1,1-dimethylethyl)-5-hydroxy-2-pyrimidinyl]-1-propanone

A solution of 8.4 g (28 mmol) of 4,6-bis(1,1-dimethylethyl)-5-hydroxy-N-methoxy-N-methyl-2-pyrimidinecarboxamide in 150 mL of tetrahydrofuran was cooled in ice and treated dropwise with 40 mL (120 mmol) of a 3.0M solution of ethylmagnesium bromide in diethyl ether. The mixture was stirred in ice for 2 hours, then at room temperature for an additional 16 hours. The reaction mixture was again cooled in ice, and excess Grignard reagent was destroyed by dropwise addition of 50 mL of saturated aqueous ammonium chloride solution. The reaction mixture was added to 400 mL of ammonium chloride solution and extracted several times with ethyl acetate. The combined organic layers were washed with brine, dried (anhydrous sodium sulfate), and evaporated. Recrystallization of the residue from hexane yielded 5.0 g (67%) of the ethyl ketone product, mp 123° C.–125° C.

$^1$H NMR (deuteriochloroform): δ 1.22 (t, 3 H, CH$_3$), 1.49 (s, 18 H, t-Bu), 3.18 (q, 2 H, CH$_2$).

Anal. Calcd. for $C_{15}H_{24}N_2O_2$:
C, 68.15; H, 9.15; N, 10.60.
Found: C, 67.93; H, 8.95; N, 10.47.

EXAMPLE 3

1-[4,6-Bis(1,1-dimethylethyl)-5-hydroxy-2-pyrimidinyl]-2-bromo-1-propanone

A suspension of 9.5 g (43 mmol) of pulverized copper (II) bromide in 30 mL of ethyl acetate was heated to reflux and treated dropwise with a solution of 5.6 g (21 mmol) of 1-[4,6-bis(1,1-dimethylethyl)-5-hydroxy-2-pyrimidinyl]-1-propanone in 30 mL of chloroform. The mixture was stirred at reflux for 2 hours, cooled, diluted with fresh ethyl acetate, and filtered. The filtrate was washed with 5% aqueous sodium bicarbonate solution and brine, then dried (anhydrous sodium sulfate), and evaporated. Purification of the residue by flash chromatography (silica gel, 0.20% methanol in dichloromethane elution) gave 6.4 g (88%) of the bromoketone product, mp 135° C.–136° C.

$^1$H NMR (deuteriochloroform): δ 1.50 (s, 18 H, t-Bu), 1.90 (d, 3 H, CH$_3$), 5.90 (q, 1 H, CH).

Anal. Calcd. for $C_{15}H_{23}BrN_2O_2$:
C, 52.49; H, 6.75; N, 8.16.
Found: C, 52.43; H, 6.68; N, 8.05.

EXAMPLE 4

2-Azido-1-[4,6-bis(1,1-dimethylethyl)-5-hydroxy-2-pyrimidinyl]-1-propanone

A solution of 1.2 g (18 mmol) of sodium azide in 9.0 mL of water was added dropwise to a solution of 5.5 g (16 mmol) of 1-[4,6-bis(1,1-dimethylethyl)-5-hydroxy-2-pyrimidinyl]-2-bromo-1-propanone in 35 mL of acetone. The mixture was stirred for 2 hours then added to 100 mL of water and extracted with ethyl acetate. The organic layers were washed with brine, dried (anhydrous sodium sulfate), and evaporated to yield 4.7 g (96%) of the azide product, mp 91° C.–92° C., suitable for further synthesis.

$^1$H NMR (deuteriochloroform) δ 1.49 (s, 18 H, t-Bu), 1.60 (d, 3 H, CH$_3$), 5.24 (q, 1 H, CH), 5.67 (broad s, 1 H, OH).

EXAMPLE 5

2-Amino-1-[4,6-bis(1,1-dimethylethyl)-5-hydroxy-2-pyrimidinyl]-1-propane monohydrochloride A solution of 4.7 g (15.4 mmol) of 2-azido-1-[4,6-bis(1,1-dimethylethyl)-5-hydroxy-2-pyrimidinyl]-1-propanone in 15 mL of methanol containing 0.80 mL of concentrated hydrochloric acid was hydrogenated over 5% palladium on carbon catalyst. At the completion of the reduction, the mixture was filtered and the filtrate evaporated to yield 2.0 g (41%) of the amine hydrochloride product, mp 193° C.–195° C., suitable for further synthesis.

$^1$H NMR (dimethyl sulfoxide-$d_6$): δ 1.43 (s, 18 H, t-Bu), 1.55 (d, 3 H, CH$_3$), 5.03 (m, 1 H, CH), 8.48 (broad s, 3 H, NH$_3^+$), 9.41 (broad s, 1 H, OH).

EXAMPLE 6

4,6-Bis(1,1-dimethylethyl)-2-(2-hydroxy-5-methyl-1H-imidazol-4-yl)-5-pyrimidinol A mixture of 1.0 g (3.2 mmol) of 2-amino-1-[4,6-bis(1,1-dimethylethyl)-5-hydroxy-2-pyrimidinyl]-1-propane monohydrochloride and 0.25 mL (4.0 mmol) of concentrated hydrochloric acid in 8.0 mL of absolute ethanol was treated dropwise with a solution of 0.41 g (6.3 mmol) of sodium cyanate in 3.5 mL of water. After stirring for 90 minutes, the precipitate was filtered and washed with a 9:1 water:ethanol solution to yield 0.93 g (97%) of crude imidazole product. A sample purified by flash chromatography (silica gel, 10% methanol in chloroform elution) had mp 282° C.–284° C.

$^1$H NMR (deuteriochloroform): δ 1.44 (s, 18 H, t-Bu), 2.50 (s, 3 H, CH$_3$), 6.48 (broad s, 1 H, pyrimidine OH), 8.18 (broad s, 1 H, imidazole OH), 10.17 (broad s, 1 H, NH).

Anal. Calcd. for $C_{16}H_{24}N_4O_2$:
C, 63.13; H, 7.95; N, 18.41.
Found: C, 62.81; H, 7.82; N, 18.08.

We claim:
1. A compound of the formula

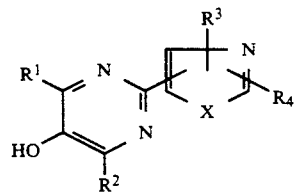

I or a pharmaceutically acceptable salt or hydrate thereof, wherein X is NH, S or O; $R_1$ and $R_2$ are each independently hydrogen or lower alkyl; $R_3$ is hydrogen, lower alkyl, phenyl, phenyl substituted by one, two, or three substituents of one or more of each of alkyl of one to four carbons, alkoxy, thioalkoxy, alkanoyloxy, carboalkoxy, in which "alk" is one to four carbons, hydroxymethyl, $NR_5R_6$ wherein $R_5$ and $R_6$ are each independently hydrogen or lower alkyl, nitro, $CF_3$, or halogen, $NR_5R_6$ in which $R_5$ and $R_6$ are as defined above, $OR_7$ or $S(O)_nR_7$ in which $R_7$ is hydrogen, lower alkyl, or phenyl and n is 0, 1, or 2; and $R_4$ is phenyl, substituted phenyl as defined above, $NR_5R_6$, $OR_7$, or $S(O)_nR_7$ in which $R_5$ and $R_6$ are as defined above.

2. A compound of claim 1 wherein $R_1$ and $R_2$ are lower alkyl.

3. A compound of claim 2 wherein $R_1$ and $R_2$ are tertiarybutyl.

4. A compound of claim 3 wherein $R_4$ is OH.

5. A compound of claim 4 which is 4,6-bis-(1,1-dimethylethyl)-2-(2-hydroxy-5-methyl-1H-imidazol-4-yl)-5-pyrimidinol.

6. A pharmaceutical composition for the treatment of inflammation which comprises an antiinflammatory effective amount of the compound of claim 1 and a pharmaceutically acceptable carrier.

7. A method of treating inflammation in a human in need of such treatment which comprises administering a composition of claim 6.

* * * * *